US00RE40626E

(19) United States
(12) Reissued Patent
Choke-arpornchai et al.

(10) Patent Number: US RE40,626 E
(45) Date of Reissued Patent: Jan. 27, 2009

(54) VOLATILE ACTIVES DISPENSER

(75) Inventors: Bunchorn Choke-arpornchai, Samutprakarn (TH); Nittayanun Korprasert, Bangkok (TH); Chadaporn Kusumarn, Bangkok (TH)

(73) Assignee: S. C. Johnson & Son, Inc., Racine, WI (US)

(21) Appl. No.: 29/256,633

(22) Filed: Mar. 22, 2006

Related U.S. Patent Documents

Reissue of:
(64) Patent No.: D. 474,268
Issued: May 6, 2003
Appl. No.: 29/159,066
Filed: Apr. 12, 2002

(51) LOC (9) Cl. ..... 23-04
(52) U.S. Cl. ..... D23/366
(58) Field of Classification Search ..... D23/366, D23/367, 368, 369; 239/52, 53, 57–59, 34, 239/60; 261/DIG. 65; 422/305, 120; 454/157, 454/156
See application file for complete search history.

(56) References Cited

U.S. PATENT DOCUMENTS

D403,420 S 12/1998 Vullion
D419,659 S 1/2000 Yang
D422,350 S 4/2000 Wu

*Primary Examiner*—Lisa P Lichtenstein

(57) CLAIM

The ornamental design for a volatile actives dispenser, as shown and described.

DESCRIPTION

FIG. 1 is a front perspective view of a volatile actives dispenser showing our new design.
FIG. 2 is a front view thereof.
FIG. 3 is a rear view thereof.
FIG. 4 is a right side view thereof.
FIG. 5 is a left side view thereof.
FIG. 6 is a top plan view thereof; and,
FIG. 7 is a bottom plan view thereof.
The broken line showing of environmental structure in FIGS. 3–7 is for illustrative purposes only and forms no part of the claimed design.

1 Claim, 2 Drawing Sheets

Figure 1:
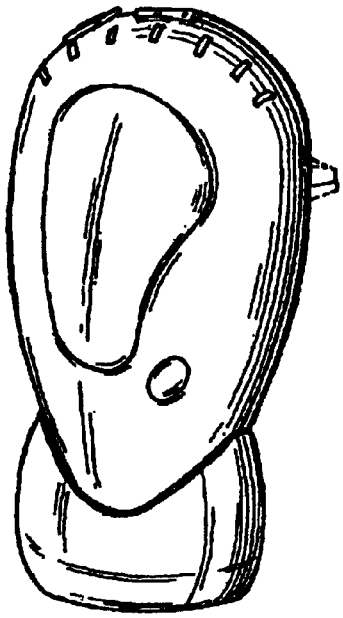
Figure 2:
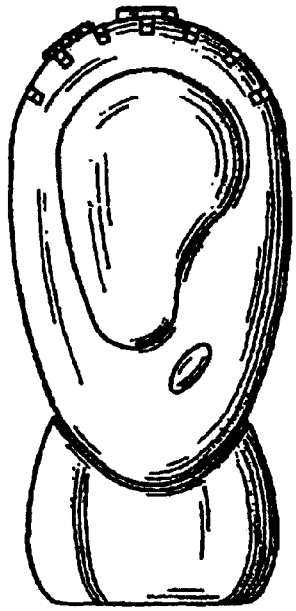
Figure 3:
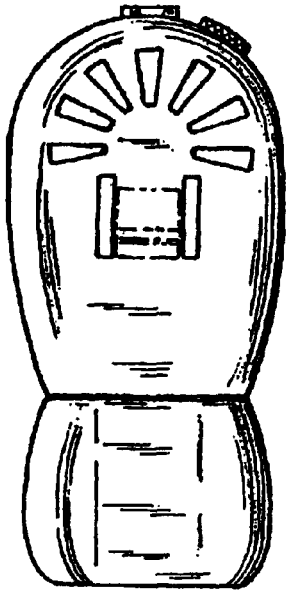
Figure 4:
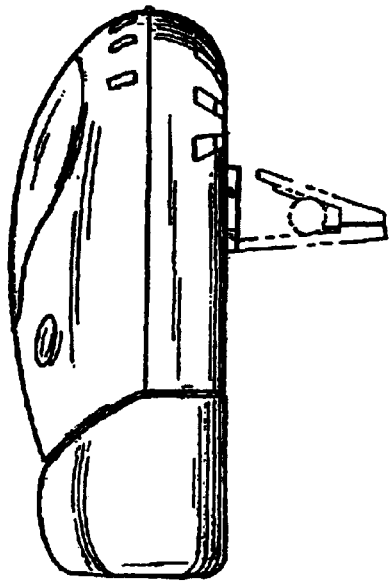
Figure 5:
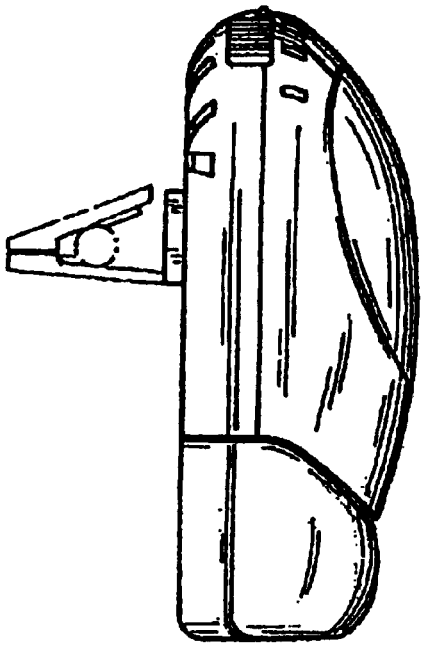
Figure 6:
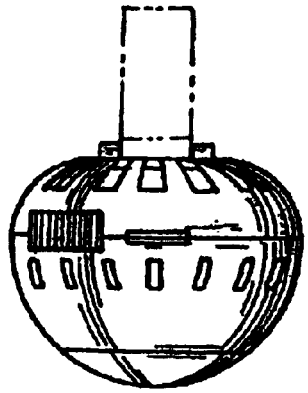
Figure 7:
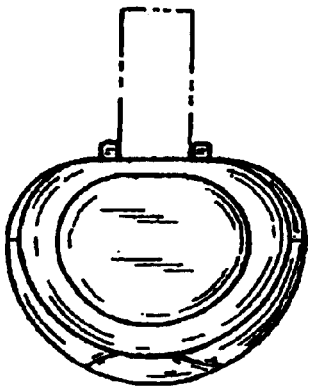

Matter enclosed in heavy brackets [ ] appears in the original patent, but forms no part of this reissue; matter printed in italics indicates the additions made by reissue.